United States Patent [19]

Cho et al.

[11] Patent Number: 5,672,170
[45] Date of Patent: Sep. 30, 1997

[54] LASER TRANSMYOCARDIAL REVASCULARIZATION ARRANGEMENT

[75] Inventors: George E. S. Cho, Hopkinton; Horace W. Furumoto, Wellesley, both of Mass.

[73] Assignee: Cynosure, Inc., Bedford, Mass.

[21] Appl. No.: 666,251

[22] Filed: Jun. 20, 1996

[51] Int. Cl.⁶ .............................. A61B 5/06; A61B 5/00; A61N 1/362
[52] U.S. Cl. .............................. 606/12; 606/11; 606/15; 607/9; 607/25
[58] Field of Search .................... 606/10–19; 607/9, 607/24, 25; 604/21, 22

[56] References Cited

U.S. PATENT DOCUMENTS

| | | | |
|---|---|---|---|
| 4,453,547 | 6/1984 | Castel et al. | 607/46 |
| 5,125,926 | 6/1992 | Rudko et al. | 606/19 |
| 5,389,096 | 2/1995 | Aita et al. | 606/15 |
| 5,411,532 | 5/1995 | Mortazavi | 607/22 |
| 5,454,807 | 10/1995 | Lennox et al. | 606/15 |
| 5,464,404 | 11/1995 | Abela | 606/15 |

OTHER PUBLICATIONS

Transmural Channels Can Protect Ischemic Tissue; Whittaker et al "Circulation" vol. 93, No. 1 Jan. 1996 pp. 143–152.

Primary Examiner—Jennifer Bahr
Assistant Examiner—David M. Ruddy
Attorney, Agent, or Firm—Don Halgren

[57] ABSTRACT

The present invention involves a system for transmyocardial revascularization of a beating heart, including a laser device for ablating wall tissue of the heart being treated, with a pacemaker connected to the heart being treated, to provide electrical signals to control the cardiac cycle of that heart, and a conditioning circuit connected to both the pacemaker and to the laser, to permit the controlled "safe period" firing of the laser. The laser includes an optic waveguide articulably arranged to irradiate the wall of the heart. The conditioning circuit is programmed to permit the firing of the laser upon the time of the cardiac cycle of the heart during a non-ventricular repolarization time period.

18 Claims, 1 Drawing Sheet

LASER TRANSMYOCARDIAL REVASCULARIZATION ARRANGEMENT

BACKGROUND OF THE INVENTION

1. Field of the Invention

This invention relates to laser systems for operating on beating hearts, and more particularly to laser systems for performing transmyocardial revascularization.

2. Prior Art

Coronary heart disease is the major cause of death in developed countries in spite of the advances in health care systems and preventative medicines. Such health care for treating coronary artery disease has included bypass surgery, and/or angioplasty. Each of these treatments have their own special areas of risk, and each are extremely expensive.

A recently developed methodology has appeared, to supplement or replace those above-identified treatments. This new methodology is called Transmyocardial Revascularization. This revascularization permits blood to be supplied to the heart through the myocardium, to replace blood which has been cut off due to a diseased coronary artery or the like, without the need, risk or expense of going through a by-pass or angioplasty procedure.

Revascularization may be done through partial open heart surgery by generating the holes or channels within that heart wall by a syringe needle, or by energization via an optical fiber coupled to a laser device.

One such laser device and control system is shown in U.S. Pat. No. 5,125,926 to Rudko et al. This particular pulsed laser system uses an ECG signal to monitor the beating of the heart being operated upon. The laser connected to the system is then synchronized to operate at a specific time based on the detection of an "R" wave in the heart's beating cycle so as to trigger a pulse of laser energy so as to effect a hole in the wall of the heart. A triggering for this device utilizes a complicated electromechanical arrangement for powering a carbon-dioxide laser and cumbersome electric lead wires physically attached to the patient's body, including a dedicated wave detection computer algorithm with its associated hardware devices. The actual detection of these particular natural heart triggering waves, such as the "R" wave, may not always be reliable, due to the weakness of that particular natural wave signal. The strength of that triggering signal is often measured in micro volts.

In these prior art devices, 40 Joules of laser energy (typical quantity needed to ablate a heart wall) is delivered in one pulse of 40 milliseconds, to create a channel in the muscular heart wall for revascularization thereof. These prior art devices however, will require a 1000 watt laser to perform such a procedure.

That revascularization procedure of a damaged heart, must also be done when that particular heart is not cycling through it's particular "T" wave on its electrocardiogram. The duration of the "T" wave cycle time is that time in a heart cycle when it is most vulnerable to fibrillation, a condition where the cardiac muscle fiber contracts asynchronously. This is when no actual cardiac output or blood flow occurs, and may otherwise be known as a "heart attack".

It is an object of the present invention to provide a laser system for performing transmyocardial revascularization upon a beating heart.

It is a further object of the present invention to provide a laser system for transmyocardial revascularization to operate in a controlled cycle of the heart's ECG, to maximize accuracy and minimize risks.

It is yet a further object of the present invention to provide a transmyocardial revascularization system which may be utilized to create cycle time-controlled bursts or continuous pulses of laser energy to provide perfusion holes or channels within the heart wall.

It is yet still a further object of the present invention, to provide a laser system for transmyocardial revascularization, which minimizes risk and expense of those systems of the prior art.

BRIEF SUMMARY OF THE INVENTION

The present invention comprises an electronic pacemaker synchronized laser system for transmyocardial revascularization. The revascularization system includes an electronic pacemaker utilized to assist the triggering of an ailing heart to maintain a satisfactory level of blood pumping volume. The pacemaker includes a pacing electrode which may be connected to the heart through a vein, which feeds into the right atrium, and then into the right ventricle. The pacing electrode may also connected to the heart via many other routes as is commonly practiced by cardiologists.

When the pacemaker is activated, electrical impulses of a certain desired preset repetitive rate are delivered to the electrode in the right ventricle, causing or forcing the whole ventricular muscle to contract. Thus, the heart is triggered, by the electronic pacemaker, so as to pump blood therethrough. Under this controlled condition, the cardiac rhythm is made to be very regular and predictable.

The electronic impulses which are used to trigger the heartbeat, are also utilized to trigger the laser excitation for the revascularization process.

The pacing signal conditioning circuit thus triggered, is utilized to set the interval and intensity at the laser control circuit. The laser control circuit triggers the laser unit which sends pulses of light energy through an optical waveguide having a distal end which may be manipulable so as to ablate holes through the target heart wall.

Since the electronic pulses from the pacemaker are utilized in triggering the heart's rhythm, and since they are also utilized to trigger the laser, the lasing action is made to occur outside of the ventricular repolarization time. This practice thus prevents the risk of laser induced heart attack or fibrillation if such laser at lasing action were otherwise to occur during the "T" wave time period of the heart's ECG.

Such a signal from the electronic pacemaker is therefore in synchrony with and controls the cardiac rhythm. That trigger signal is high enough of a voltage, usually thousands of times higher than the heart's own natural "R" wave, which may be measured only in micro volts, and which is the triggering signal for prior art laser revascularization devices. Since this electronic pacemaker generated trigger signal is very reliable, delivery of laser pulses at only safe periods of time in the cardiac cycle is insured.

The delivery of electronic pacemaker triggered laser pulses need not be limited to one pulse per cardiac cycle, as is found in the prior art devices. The pacing signal conditioning circuit may require the laser control circuit to fire multiple laser pulses before ventricular relaxation of the "T" wave portion of the ECG cycle occurs. Therefore, a channel or hole in the heart wall may be ablated by the laser with multiple pulses or a hole may be ablated by a long duration of a continuous wave laser pulse. Since multiple pulses or a longer continuous wave may be produced, a lower power laser device may be utilized, to drastically reduce the cost of both the system and the surgical procedure.

In the present invention, the physician operating the system is allowed a much longer time window to lase the heart at one particular location, because the heart cycle is forced beat in a preset and timed period. When a heart is paced by the electronic pacemaker as contemplated by the present invention, for example, at about 80 beats per minute, the time period between each successive heart beat is 750 milliseconds. The "T" wave time (the heart's most vulnerable time) occurs about 50–350 milliseconds after the "R" wave on the heart's ECG cycle. This permits a time period of about 400 milliseconds for ablating of the heart wall by the laser device of the present invention. With a laser pulsing at 200 Hz (time period between two pulses=five milliseconds) we have 400 milliseconds divided by five milliseconds which equals 80 pulses that can be delivered to ablate one channel.

Since the physician has that longer time window available to lase the heart at one location, due to its cardiac cycle being forced to fit in the preset and fixed time period, the laser power needed to deliver the energy required for this function need only be about 100 watts to 150 watts, which is about ¹⁄₁₀th the power needed in the prior art device. 40 Joules has been determined by practitioners in the field, to be the amount of energy typically needed to ablate heart wall tissue. To obtain 40 J of total energy to ablate such tissue, each laser pulse therefore needs to be 40 J divided by the number of pulses per ablation, such as 80 pulses, which energy therefore equals 0.5 J per pulse. Alternatively, the laser unit may be energized in a continuous wave mode, and that 40 J of energy may be delivered in an interval of up to 400 milliseconds long. The size of the laser for such a continuous requirement is 40 J divided 0.4 seconds, which also equals 100 watts of laser power.

The invention thus comprises a pacemaker synchronized laser system for performing transmyocardial revascularization of a beating heart, including a laser device having an articulable laser pulse delivery conduit, an electronic pacemaker connected to a heart to be treated to control the cardiac rhythm of the heart, and a control circuit connected to both the pacemaker and to the laser, to permit laser activation at specific predetermined intervals, to permit the laser pulse delivery conduit to fire at and ablate a wall portion of the heart being treated only during those safe specific pacemaker controlled intervals. The laser may be arranged to pulse at a rate of 1 pulse or more per channel for tissue ablation. If of course, a higher power laser is utilized, the pacemaker may be used to deliver 1 pulse to ablate the wall of the heart.

The laser delivery conduit comprises a flexible optical waveguide to deliver laser energy to the wall of the heart, from the inside thereof. The laser delivery conduit may also comprise a flexible optical waveguide or articulated arm to deliver laser energy through the wall of the heart, from the outside of the heart. The pacemaker controls both the cardiac rhythm and the laser timing to eliminate laser energization and hence heart malfunctioning during the ventricular repolarization period of the heart being treated. The invention includes a method of performing transmyocardial revascularization on a beating heart, by a laser device, comprising the steps of: attaching an electronic pacemaker to the beating heart by a connective lead; connecting a conditioning circuit to the electronic pacemaker and also to a laser device having an articulable optic waveguide connected thereto, so as to control the firing of the laser upon the controlled beating of the heart being treated; aiming the laser output of the optical waveguide at the walls of the beating heart being treated; and controllably energizing the laser to ablate a channel into the wall of the beating heart being treated during a period of the cardiac cycle except during the "T" wave period of that cycle. The method of the present invention includes the steps of: pulsing the laser by one or more pulses per channel to ablate into the wall of the heart being treated to allow minimizing of the power requirements needed by the laser device, and powering the laser device to about 100 watts; energizing the laser for a continuing pulse of about at least 100 milliseconds; introducing the pacing lead of the pacemaker through a vein and into the right atrium and then the right ventricle, for conductive connection to the heart being treated; energizing the laser device to ablate a channel in the wall of the heart being treated after a time interval of about 350 milliseconds from the "R" wave of the cardiac cycle; or energizing the laser device to ablate a channel in the wall of the heart being treated, during a time period of about 400 to 450 milliseconds immediately before the "R" wave of the cardiac cycle; triggering such energization of the laser upon the detection of a condition by the conditioning circuit of the cardiac cycle, to a non "T" wave signal; and ablating the wall of the heart outside of that ventricular repolarization ("T" wave period) time period of the heart's cardiac cycle.

The invention also includes a system for transmyocardial revascularization of a beating heart, comprising: a laser device for ablating wall tissue of the heart being treated, a pacemaker connected to the heart being treated, to provide electrical signals to control the cardiac cycle of that heart, a conditioning circuit connected to the pacemaker and to the laser, to control the firing of the laser, the laser including an optical waveguide articulately arranged to irradiate the wall of the heart, the conditioning circuit programmed to fire the laser upon the cardiac cycle of the heart during a non-ventricular repolarization time period.

Thus what has been shown is a system for the performing of transmyocardial revascularization which may be performed at any time during a pacemaker controlled cycle so as to avoid the time during that cycle of ventricular repolarization (the "T" wave period), where the heart is in the most vulnerable state, and wherein any electrical or mechanical stimulation may cause that heart to fibrillate, a condition where each cardiac muscle fiber contracts asynchronously. By such electronic pacemaker control, the actual pulsing of the laser to perforate a heart wall may be very accurately controlled.

BRIEF DESCRIPTION OF THE DRAWINGS

The objects and advantages of the present invention will become more apparent, when viewed in conjunction with the following drawings, in which.

DESCRIPTION OF THE PREFERRED EMBODIMENT

Figure 1:
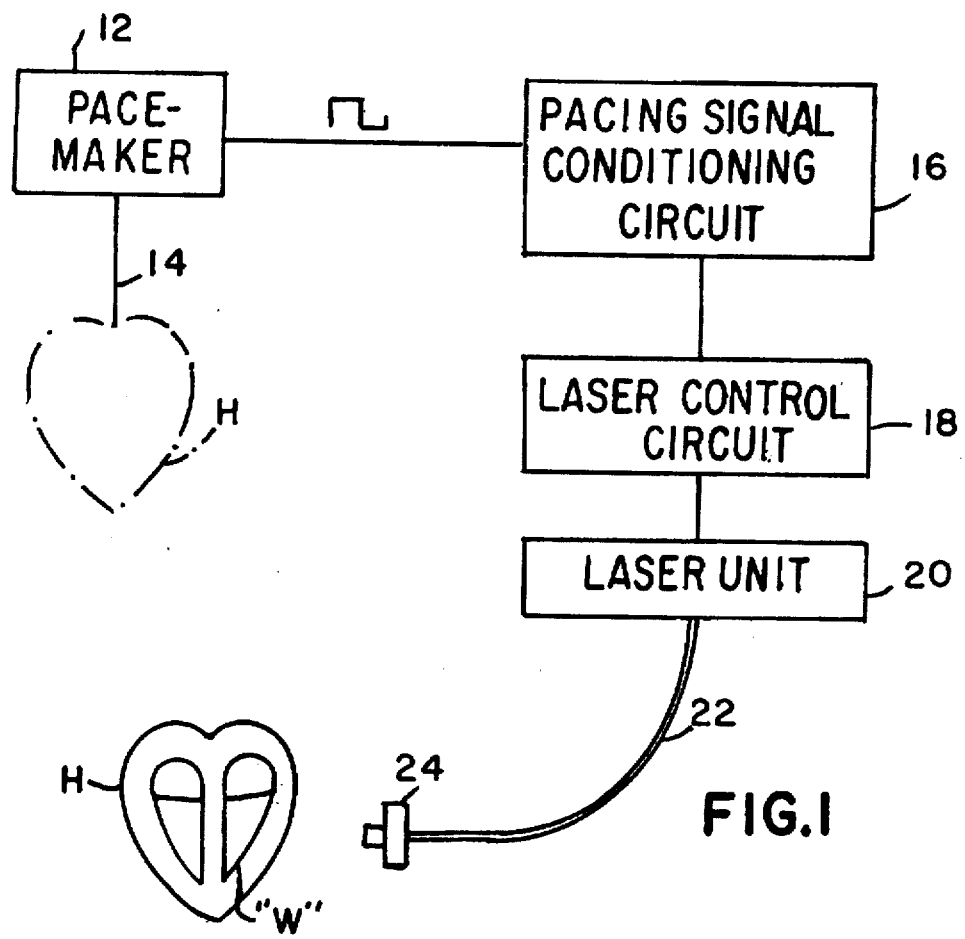
FIG. 1 is a schematic block diagram of a pacemaker controlled transmyocardial revascularization system.

The present invention comprises an electronic pacemaker synchronized laser system for transmyocardial revascularization as shown in FIG. 1. The revascularization system 10 includes an electronic pacemaker 12 utilized to assist the triggering of an ailing heart to maintain a satisfactory level of blood pumping volume. The pacemaker 12 includes a pacing electrode 14 which is connected to the heart "H" through a vein, which feeds into the right atrium, and then into the right ventricle. The pacing electrode may also be connected to the heart via many other routes known in the art. When the pacemaker 12 is activated, electrical impulses of a certain desired, preset repetitive rate are delivered to the electrode 14 in the right ventricle, causing or forcing the whole ventricular muscle to contract. Thus, the heart "H" is triggered, by the electronic pacemaker 12, so as to pump blood therethrough. Under this controlled condition, the cardiac rhythm is made to be very regular and predictable.

The electronic impulses which are used to trigger and control the heartbeat, are also utilized to trigger the laser excitation for the revascularization process through a pacing signal conditioning circuit 16. The pacing signal conditioning circuit 16 includes programmable chips to permit regulation and control over timing and power activities of the system 10.

The pacing signal and conditioning circuit 16 thus triggered, is utilized to set the interval and intensity at a laser control circuit 18. The laser control circuit 18 regulates the laser device 20 (such as a Carbon Dioxide laser, an Erbium YAG laser, or a Holmium YAG laser), which sends pulses of light energy through an articulable waveguide 22 having a distal pulse delivery end 24 which is manipulable so as to lase holes through the wall "W" of the target heart "H".

Since the electronic pulses from the pacemaker 12 are used in triggering the heart "H", and since they are used to trigger the laser device 20, the lasing action is made to occur outside of the heart's vulnerable ventricular repolarization time. This practice thus prevents the risk of laser induced heart attack or fibrillation if such lasing action were otherwise to occur during that vulnerable "T" wave time period of the heart's ECG.

The electronic pacemaker 12, is therefore in synchrony with and controls the cardiac rhythm. The trigger signal through the pacemaker 12 is of a high enough a voltage, usually thousands of times higher than the heart's own natural "R" wave, which natural "R" wave may be measured only in "difficult to accurately identify" micro volts (or millivolts), and which natural "R" wave is the triggering signal for prior art laser revascularization devices. Since this electronic pacemaker generated trigger signal of the present invention is very reliable, delivery of laser pulses at only safe periods of time in the cardiac cycle is insured, by this new invention.

The delivery of electronic pacemaker triggered laser pulses of the present invention need not be limited to one pulse per cardiac cycle, as is found in the prior art devices. The pacing signal conditioning circuit 16 of the present invention may allow the laser control circuit 18 to fire multiple laser pulses before or after the critically risky ventricular relaxation period occurs, which period is the "T" wave portion of the ECG cycle. Therefore, a channel or hole in the heart wall may be ablated by the laser 20 with multiple pulses or a hole may be ablated by a long duration of a continuous wave laser pulse via the articulated arm or optical waveguide 22 and lens 24. Since multiple pulses or a longer continuous wave may be produced during the managed, electronic pacemaker controlled cycle, a lower power laser device may be utilized, (of the order of 1/10th the power required of the prior art devices) to drastically reduce the cost of both the system and the surgical procedure. However, if a higher power laser is utilized, the present invention will provide a reliable triggering means for such system.

Figure 2:
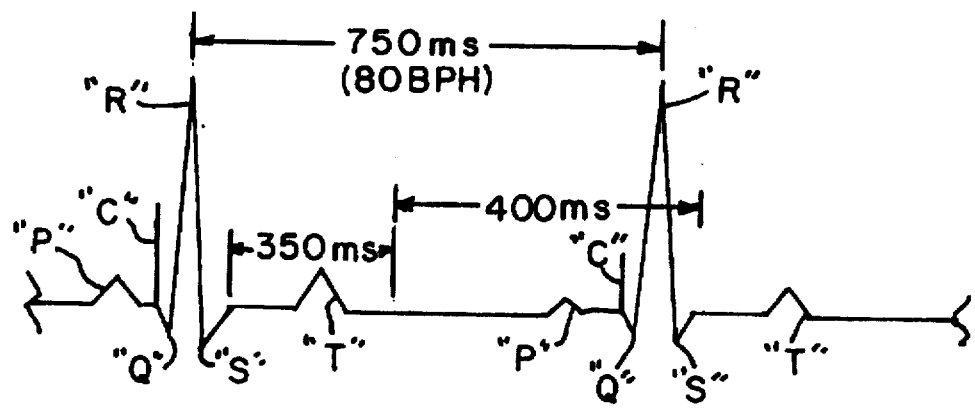
FIG. 2 is an illustration of an ECG signal showing the sequential P, Q, R, S, and T pulses thereon.

In the present invention, the physician operating the system is allowed a much longer time window to lase the heart at one particular site of its wall "W", because the heart cycle is forced beat in a preset and timed period. When a heart is paced by the electronic pacemaker as contemplated by the present invention, for example at about 80 beats per minute, the time period between each successive heart beat is 750 milliseconds. The "T" wave time (the heart's most vulnerable time) occurs usually about 50–350 milliseconds after the "R" wave on the heart's ECG cycle. Such an ECG cycle is represented in FIG. 2, showing the P, Q, R, S, and the critical "T" waves. This paced cycle permits a time period of about 400 milliseconds for lasing of the heart wall by the laser device of the present invention. With a laser pulsing at 200 Hz (time period between two pulses=five milliseconds) we have 400 milliseconds divided by five milliseconds which equals 80 pulses that can be delivered to ablate one channel. To obtain the typical 40 J of total energy for heart wall ablation, each laser pulse needs to be 40 J divided by the number of pulses, typically 80 pulses, which therefore equals 0.5 J per pulse. The laser requirements needed to deliver this energy is about 100 Watts to 150 Watts power, which is about 1/10 of the power required in prior art devices. Alternatively, the laser unit may be energized in a continuous wave mode, and the 40 J of energy can be delivered in 400 milliseconds. The size of the laser for such a requirement is 40 J divided 0.4 seconds, which also equals 100 Watts of laser power. Such a pacer artifact "C" can be initiated by a predetermined signal, shown at for example "C" in the cycle, in FIG. 2, to permit lasing during any time during that 400 millisecond window.

Thus what has been shown is a system for the performing of transmyocardial revascularization which revascularization may be performed at any "safe" time during a pacemaker controlled cycle to avoid that time during its cycle, of ventricular repolarization (the "T" wave period), where the heart is in the most vulnerable state, and wherein any electrical or mechanical stimulation may cause that heart to fibrillate, a condition where each cardiac muscle fiber contracts asynchronously. By such electronic pacemaker control, the actual pulsing of the laser to ablate a heart wall may be very accurately controlled.

We claim:

1. A pacemaker synchronized laser system for performing transmyocardial revascularization of a beating heart, comprising:

a laser device having a laser energy delivery conduit;

an electronic pacemaker for connection to a heart to be treated, to control the cardiac rhythm of a heart to be treated; and a control circuit connected to both said pacemaker and to said laser device, to activate said laser device at specific predetermined intervals, to permit said laser energy delivery conduit to ablate a portion of a wall of a heart being treated only during certain safe specific pacemaker controlled intervals.

2. The pacemaker synchronized laser system as recited in claim 1, wherein said laser device is arranged to pulse at a rate of at least 2 pulses per channel ablation.

3. The pacemaker synchronized laser system as recited in claim 1, wherein said laser delivery conduit comprises a flexible optical conduit to deliver laser energy to said wall portion of a heart being treated, from the inside thereof.

4. The pacemaker synchronized laser system as recited in claim 1, wherein said laser device comprises a flexible articulable optical conduit to deliver laser energy through said wall portion of a heart being treated, from the outside thereof.

5. The pacemaker synchronized laser system as recited in claim 1, wherein said pacemaker controls both the cardiac rhythm and the laser timing to eliminate laser energization during ventricular repolarization period of the cycle of a heart being treated.

6. A method of performing transmyocardial revascularization on a beating heart, by a laser device, comprising the steps of:

attaching an electronic pacemaker by a connective lead, to a beating heart being treated;

connecting a conditioning circuit to said electronic pacemaker and also to a laser device having an optical conduit so as to control the firing of said laser device based upon the controlled beating of a heart being treated;

aiming the laser device output from said optical conduit at the wall of a beating heart being treated; and controllably energizing said laser device to ablate a channel into the wall of a beating heart being treated during a period of the cardiac cycle which excludes the "T" wave period of that cycle.

7. The method of claim 6, including the step of:

pulsing said laser device by at least 2 pulses per channel to ablate into the wall of a heart being treated, to minimize the power requirements needed by said laser device.

8. The method of claim 7, including the step of: powering said laser device to about 100 watts.

9. The method of claim 6, including the step of:

energizing said laser device for a continuing pulse of about at least 100 milliseconds.

10. The method of claim 6, including the step of:

introducing said connective lead of said pacemaker through a vein and into the right atrium and then the right ventricle of a heart being treated, for conductive connection to a heart being treated.

11. The method of claim 6, including the step of:

energizing said laser device to ablate channel in the wall of the heart being treated, after a time interval of about 350 milliseconds from the "R" wave of the cardiac cycle.

12. The method of claim 6, including the step of:

energizing said laser device to ablate a channel in the wall of a heart being treated, during a time period of about 400 milliseconds immediately before the "R" wave of the cardiac cycle.

13. The method of claim 6, including the step of:

triggering the energization of said laser device upon the detection of a condition by the conditioning circuit, of the cardiac cycle to a non "T" wave signal.

14. The method claim 6, including the step of:

lasing a heart being treated outside of the ventricular repolarization time period of its cardiac cycle.

15. A system for transmyocardial revascularization treatment of a beating heart, comprising:

a laser device for ablating wall tissue of a heart being treated;

an electronic pacemaker for connection a heart being treated, to provide electrical signals to control the cardiac cycle of that heart;

a conditioning circuit connected to said pacemaker and to said laser device, to control the firing of said laser device, said conditioning circuit programmed to permit said laser device to fire upon the reaching of a safe period in the controlled cardiac cycle of a heart being treated such as occurs during a non-ventricular repolarization time period.

16. The system for transmyocardial revascularization, as recited in claim 15, wherein said pacemaker triggers the firing of said laser device by the sending of a proper triggering signal thereto.

17. The system for transmyocardial revascularization, as recited in claim 15, wherein said laser device includes an optical waveguide aimably arranged to irradiate the wall of a heart being treated.

18. The system for transmyocardial revascularization, as recited in claim 15, wherein said laser device includes an articulable arm arranged to irradiate the wall of a heart being treated.

* * * * *